US012620495B2

(12) United States Patent
Bulut et al.

(10) Patent No.: US 12,620,495 B2
(45) Date of Patent: May 5, 2026

(54) SYSTEM AND METHOD FOR CONFIGURING DATA COLLECTION FOR A DIGITAL TWIN

(71) Applicant: KONINKLIJKE PHILIPS N.V., Eindhoven (NL)

(72) Inventors: Murtaza Bulut, Eindhoven (NL); Lieke Gertruda Elisabeth Cox, Eindhoven (NL); Cornelis Petrus Hendriks, Eindhoven (NL); Valentina Lavezzo, Heeze (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 237 days.

(21) Appl. No.: 17/785,103

(22) PCT Filed: Dec. 17, 2020

(86) PCT No.: PCT/EP2020/086860
§ 371 (c)(1),
(2) Date: Jun. 14, 2022

(87) PCT Pub. No.: WO2021/123045
PCT Pub. Date: Jun. 24, 2021

(65) Prior Publication Data
US 2023/0027455 A1    Jan. 26, 2023

Related U.S. Application Data

(60) Provisional application No. 62/949,465, filed on Dec. 18, 2019.

(30) Foreign Application Priority Data

Jan. 6, 2020    (EP) .................................... 20150333

(51) Int. Cl.
*G16H 50/50*        (2018.01)

(52) U.S. Cl.
CPC .................................. *G16H 50/50* (2018.01)

(58) Field of Classification Search
None
See application file for complete search history.

(56) References Cited

U.S. PATENT DOCUMENTS

2017/0172434 A1    6/2017    Amelard
2017/0286572 A1*  10/2017    Hershey .................... B64F 5/60
(Continued)

FOREIGN PATENT DOCUMENTS

WO    WO-2019005184 A1 *  1/2019    ............. G16H 10/60

OTHER PUBLICATIONS

Bjornsson, B., Borrebaeck, C., Elander, N., Gasslander, T., Gawel, D. R., Gustafsson, M., . . . Benson, M. (2019). Digital twins to personalize medicine. Genome Medicine, 12(1), Article No. 4. doi:http://dx.doi.org/10.1186/s13073-019-0701-3 (Year: 2019).*
(Continued)

*Primary Examiner* — Emily Huynh

(57) ABSTRACT

A system (10) for configuring data collection for provision to a digital twin for generating a desired set of output information (e.g. physiological or anatomical parameter estimations) from the digital twin. The system is configured to detect available sources (56) of physical sensor data (58) pertaining to a patient, and to compare these with determined input data requirements of a digital twin (32) of the patient for computing a particular defined set of required output information. Depending on the result, a virtual sensing module (28) can be used to generate supplementary 'virtual' sensor data to compensate for any insufficiencies in the available physical sensor data or augment the physical sensor data, and the system can re-configure operating
(Continued)

settings of the available physical sensors (56) to optimally meet the input data requirements of the digital model.

14 Claims, 3 Drawing Sheets

(56) References Cited

U.S. PATENT DOCUMENTS

| 2019/0087544 A1* | 3/2019 | Peterson | G16H 50/20 |
| 2019/0321553 A1* | 10/2019 | Grosman | A61M 5/1723 |
| 2020/0135320 A1* | 4/2020 | Vleugels | G06F 3/017 |

OTHER PUBLICATIONS

Charara, S. "Your doctor could soon be treating your virtual twin as a digital patient". http://www.wareable.com/health-and-wellbeing/doctor-virtual-twin-digital-patient-ucl-887. (2015).
Gonzalez, D. et al., "Computational Patient Avatars for Surgery Planning". F. Ann Biomed Eng (2016) 44:35.
Rama, R.R. et al., "Towards real-time cardiac mechanics modelling with patient-specific heart anatomies." Computer Methods in Applied Mechanics and Engineering (2018) 328; 47-74.
Hoekstra, A.G. et al., "Virtual Physiological human 2016: translating the virtual physiological human to the clinic." The Royal Society Publishing (2018). https://royalsocietypublishing.org/doi/pdf/10.1098/rsfs.2017.0067.
Neal, M.L. et al., "Current progress in patient-specific modeling". Briefings in Bioinformatics, vol. 11, No. 1, pp. 111-126.
Liu, L. et al., "Virtual sensing techniques and their applications", IEEE International conference on networking, sensing, and control. Okayama, Japan, Mar. 26, 2009.
Dunleavy, K. "Which core body temperature measurement is most accurate?", Nursing, vol. 40, issue 12, p. 18-19, Dec. 2010. https://journals.lww.com/nursing/Fulltext2010/12000/Which_core_body_temperature_measurement+method_is.7.aspx.
Mendelson, Y. et al., "Noninvasive pulse oximetry utilizing skin reflectance photoplethysmography". IEEE Transactions on Biomedical Engineering, vol. 35, No. 10, Oct. 1988.
Cuddy, J.S. et al., "Skin temperature and heart rate can be used to estimate physiological strain during exercise in the heat in a cohort of fit and unfit males." Military Medicine, 178, 7:e841, 2013.
International Search Report for PCT/EP2020/086860 filed Dec. 17, 2020.

\* cited by examiner

SYSTEM AND METHOD FOR CONFIGURING DATA COLLECTION FOR A DIGITAL TWIN

CROSS-REFERENCE TO PRIOR APPLICATIONS

This application claims the priority benefit under 35 U.S.C. § 371 of International Patent Application No. PCT/EP2020/086860, filed on Dec. 17, 2020, which claims the priority benefit of U.S. Patent Application No. 62/949,465, filed Dec. 18, 2019 and European Patent Application No. 20150333.1, filed on Jan. 6, 2020, the contents of which are herein incorporated by reference.

FIELD OF THE INVENTION

This invention relates to the field of personal digital models (digital twins) and in particular to a system and method for configuring data collection for supplying to a digital model to obtain a set of output information from the model.

BACKGROUND OF THE INVENTION

A recent development in technology is the so-called digital twin concept. In this concept, a digital representation (the digital twin) of a physical system is provided and connected to its physical counterpart, for example through the Internet of things as explained in US 2017/286572 A1. Through this connection, the digital twin typically receives data pertaining to the state of the physical system, such as sensor readings or the like, based on which the digital twin can predict the actual or future status of the physical system, e.g. through simulation, as well as analyze or interpret a status history of the physical twin. In case of electromechanical systems, this for example may be used to predict the end-of-life of components of the system, thereby reducing the risk of component failure as timely replacement of the component may be arranged based on its end-of-life as estimated by the digital twin.

Such digital twin technology is also becoming of interest in the medical field, as it provides an approach to more efficient medical care provision. For example, the digital twin may be built using imaging data of the patient, e.g. a patient suffering from a diagnosed medical condition as captured in the imaging data, as for instance is explained by Dr Vanessa Diaz in https://www.wareable.com/health-and-wellbeing/doctor-virtual-twin-digital-patient-ucl-887 as retrieved from the Internet on 22 Oct. 2019. Such a digital twin may serve a number of purposes. Firstly, the digital twin rather than the patient may be subjected to a number of virtual tests, e.g. treatment plans, to determine which treatment plan is most likely to be successful to the patient. This therefore reduces the number of tests that physically need to be performed on the actual patient.

The digital twin of the patient for instance further may be used to predict the onset, treatment or development of such medical conditions of the patient using a patient-derived digital model, e.g. a digital model that has been derived from medical image data of the patient.

In this manner, the medical status of a patient may be monitored without the routine involvement of a medical practitioner, e.g. thus avoiding periodic routine physical checks of the patient. Instead, only when the digital twin predicts a medical status of the patient indicative of the patient requiring medical attention based on the received sensor readings may the digital twin arrange for an appointment to see a medical practitioner to be made for the patient. This typically leads to an improvement in the medical care of the patient, as the onset of certain diseases or medical conditions may be predicted with the digital twin, such that the patient can be treated accordingly at an early stage, which not only is beneficial to the patient but can also reduce (treatment) costs. Moreover, major medical incidents that the patient may be about to suffer may be predicted by the digital twin based on the monitoring of the patient's sensor readings, thereby reducing the risk of such incidents actually occurring. Such prevention avoids the need for the provision of substantial aftercare following such a major medical incident, which also alleviates the pressure on a healthcare system otherwise providing such aftercare.

A digital model may be derived based at least in part on medical image data for the patient. The digital model may additionally or alternatively be derived based on physiological sensor data (including e.g. vital signs such as heart rate, respiration rate, skin temperature) and/or from psychological patient data inferred or computed from sensor data and/or medical history data. Medical history data may also include for instance subjective patient data, for example collected by means of a questionnaire, or patient feedback.

A digital twin may be used to simulate a new physical situation or state in a patient using input physical sensor data, for example each time new information or data becomes available, e.g. when a parameter has changed as detected with a sensor or user input. The result is a new output variable field or distribution in a set of output parameters.

In some applications it may be useful to update a digital twin in real time or intermittently based for example on sensor data such that it accurately represents a real physical state of the patient. This may be useful for example during surgery or other medical procedure during which real-time estimations of patient parameters would be of use.

A digital twin typically permits different possible output information about the physical twin to be derived and extracted dependent upon what particular input information can be provided to the twin to update it or to run a suitable simulation on the twin. To derive a particular measurement or prediction or parameter from the digital twin there may be a particular set of input information required to be provided to the digital twin.

The requisite information can then be obtained from associated physical sensors and the desired output information derived.

However, the use of physical sensors is limited by certain constrains, such as: (i) power and lifetime, (ii) performance and robustness, (iii) achievable sampling frequency, precision, or signal to noise ratio, and (iii) match to the measured physical object (e.g. comfort of the human subject).

Depending on the required output information, in some cases the available physical sensors in a system may not be able to provide the necessary input information to the digital twin to enable the output to be computed.

This may happen for example when physical sensors are already being operated on a full capacity setting (e.g. maximum sampling frequency, maximum accuracy), while the (updated) digital twin requires input data with higher sampling rates and higher accuracy in order to generate the desired output information, for instance due to the need to update its bio-physical models with sufficient frequency or precision.

In further examples, it may happen that a physical sensor collecting input data for a digital twin malfunctions or becomes temporarily unavailable (e.g. develops a fault, is improperly used, becomes hacked, or becomes disconnected from the system). The typical approach in such situations would be to wait until the sensor is back on-line and to pause running of the digital twin operations. However, where the digital twin is being used in real-time to generate measurement or patient parameter information for immediate use, this is not a suitable option. This has traditionally made digital twin approaches unreliable, and other backup measures have to be put in place for critical operations.

Another problem with digital twin use for estimating patient measurements or parameters is that, because a digital twin is a dynamically updating model, its data input requirements may change as the physical situation of the patient changes. In some cases, for example the (updated) digital twin may require a new type of data, which existing physical sensors are not able to supply.

Improved digital twin based systems would therefore be of advantage which are able to remedy one or more of the above problems.

SUMMARY OF THE INVENTION

The invention is defined by the independent claims. The dependent claims define advantageous embodiments.

According to examples in accordance with an aspect of the invention, there is provided a system, comprising:

a processor arrangement communicatively coupled to a data storage arrangement storing a digital model of at least part of an anatomy of a patient; the digital model being configured for simulating a physical state of said at least part of the anatomy based on adjustment of a set of one or more model input parameters, and the model operable to provide output information related to the simulated physical state of the anatomy;

the processor arrangement communicatively coupleable in use with one or more physical sensors to receive physical patient sensor data;

the processor arrangement including a virtual sensing module configured in use for generating supplementary data;

the processor arrangement being configured in use to:

determine information indicative of currently available physical patient sensor data from physical sensors;

determine from the digital model a required set of input information for providing to the digital model in order to obtain, from the digital model, a particular defined set of output information from the model;

perform a comparison of the required set of input information and the available physical patient sensor data;

based on a result of the comparison, use the virtual sensing module to generate supplementary data to supplement or replace the physical patient sensor data, and to adjust one or more operation settings of the one or more physical sensors, for improving a match between the available physical patient data and the required set of input information.

The digital model can be described as a bio-physical model, or a machine learning algorithm, or a combination of these. In all cases, the input and outputs are pre-defined. One can consider an indexed database to determine which inputs can be used to generate what output. The characteristics of the output (e.g. accuracy, confidence interval) are then further used as an input to a mathematical function to determine further input characteristics such as required amount of data, maximum noise level, sampling frequency, frequency of collection, etc. As further explained below, the technical features and technical purposes of the digital model relate to the (best) use of physical sensor (resources), as well as speed, cost and efficacy of health services.

Embodiments of the invention have various technical effects and technical purposes. The technical effects can be defined with respect to the physical sensors' characteristics, such as improving the lifetime, battery duration, reducing sensor temperature (overheating prevention), power consumption etc.

physical sensor operation, minimizing the time to collect the needed data, and collecting high quality of data (by selectively deciding when and how to use the sensors)

physical sensor and patient interaction, such as minimizing the discomfort to the patient, e.g. preventing unnecessary wakes due to blood pressure cuff measurements.

The technical purposes relate to problems linked to the use of the physical sensors (e.g. lifetime, overheating, drift in accuracy, noise, time and expertise needed to attached and use physical sensors, making the most effective use of limited number of resources (physical sensors)), and our solution addresses these problems by selecting and operating the physical sensors.

Moreover, the digital model helps for making the right diagnosis, and selecting the right treatment, which have the following technical purposes:

reducing length of stay in hospital reduce cost of hospital stay, medications, personnel provide better guidance to clinicians which will result in them treating the patient more effectively, and therefore increase the number of patients they can treat at the same time.

The notion supplementary data refers to one of inputs of the digital model. It is referred to as supplementary to emphasize that its use is determined based on characteristics and availability of physical sensors and output needs and digital model characteristics. There may be instances that only data from physical sensors are used. Supplementary data is defined as a data synthesized from the physical sensor data. It can be a time domain signal generated by processing one of multiple physical sensor signals, as well as features extracted from the physical sensor signals.

The virtual sensor module may be configured to generate the supplementary data based at least in part on processing of received physical sensor data. Alternatively, it may be derived a different way.

The solutions proposed by embodiments of the present invention are based on dynamically configuring data generation and acquisition configurations of the system based on detected input information requirements for the digital model, in order to, in real time, better meet the information requirements.

In particular, a virtual sensing module is provided which can generate supplementary data, or hereinafter alternatively called virtual (sensor) data, for example on a temporary basis, which can supplement or compensate any gaps in the input information requirements of the digital model due to insufficiency of data provided by traditional physical sensors, or augment available physical sensor data for improved results. This can be based at least in part on processing collected physical sensor data using algorithms configured for computing further measures or estimations from the physical sensor data. It can also be based on other sources of data including for instance previously generated virtual data.

In some cases, the virtual sensor data may fully replace physical sensor data, for instance to reduce power consumption from the physical sensors, or to enable physical sensor resources to be freed up for another purpose.

Further to this, embodiments of the invention may additionally or alternatively dynamically adjust settings of connected physical sensors so as to configure the incoming physical data set to better match the input information requirements of the digital twin. Adjustable operation settings of the physical sensors might include sensor sampling rate (i.e. frequency of measurement acquisition), sensor precision or accuracy level and/or sensor activation/deactivation (i.e. turning individual sensors ON/OFF). The system is therefore able, based on detected input information needs for the digital model, to curate the particular patient dataset which is provided to the digital model for generating the desired set of output information.

Adjustment of the physical sensor settings may be performed also with reference to one or more optimization criteria or constraints. The optimization criteria may take different forms. They may include criteria for improving efficiency of the system, for instance by minimizing the number of active sensors and the rate of data collection while still meeting the input information requirements. This may save power and processing resource.

The criteria for adjustment may be defined by the output (type, accuracy, confidence level) needs, physical sensor characteristics and availability, and virtual sensing capabilities. Adjustment of physical sensors may include selecting which sensors to use, turning sensors on/off, monitoring state of sensors, determining the quality, amount, timing, and frequency of data collection, interaction of the physical sensor with the user, etc.

Embodiments of the invention thus provide a system and method for configuring data collection for provision to a digital twin for generating from the digital twin a desired set of output information, for example estimations or measures of one or more physiological or anatomical parameters.

These developments enable the system to address the problems outlined above. In particular, in some instances, in case one or more physical sensors falls off line due to a fault, the virtual sensing module may (temporarily) generate virtual data replacing the broken sensor data to prevent disturbing digital model operations. Furthermore, in case the digital model, as it develops with the physical scenario of the patient, develops changes in its required input information, the system can automatically detect this and is configured to accordingly make changes or adjustments to the total set of data (physical sensor and virtual sensor data) that is provided to the digital model, in the manner discussed above. For example, virtual sensor data might be generated, e.g. temporarily until a new or additional physical sensor can be brought online, or a sampling frequency of one or more of the sensors might be increased to provide extra data for instance.

The digital model referred to above may be a personalized digital model for a patient, i.e. a digital twin for the patient. The terms digital model and digital twin may be used interchangeably in this disclosure. Descriptions for building and operating a suitable digital model, for example comprising one or more bio-physical models, will be outlined in greater detail to follow.

The digital model may be configured to run one or more simulations to generate the output information. The processor arrangement may be configured to determine from the digital model a required set of input information for providing to the digital model in order to obtain, based on running simulations on the digital model, a particular defined set of output information from the model.

Determining the currently available sources of physical data may be based on detecting which sensors are connected to the processor arrangement and may also include detecting settings or parameters of the sensors, such as available precision, and/or available measurement sampling frequency.

The information pertaining to available patient sensor data may relate to which types of sensor data are available and optionally also a quality measure of the data which is available, such as sampling rate and/or precision level and/or signal to noise ratio of the available sources of data.

The steps performed by the processor arrangement (outlined above) may be run recurrently or repeatedly, and wherein in each 'run', based on performance of the system in generating the required output information (e.g. determined by a comparison between output data and the particular required output data) and/or in meeting the required input information requirements, adjustments may be made to the virtual sensor data that is generated and to the operation settings of the physical sensors.

The processor arrangement referred to above may comprise a plurality of processor components, or may comprise a single central processor which performs all functionality of the processor arrangement. The virtual module may be a separate processing component or may represent merely a particular functionality performed by a shared or central processing component. It may therefore be a figurative or functional module.

Although not specified above, in accordance with one or more embodiments, the processor arrangement may be further configured to generate output information from the digital model using a combination of the physical sensor data and any virtual sensor data as input information to the digital model. In other words, in use, the system, once the input data adjustments are made, may perform the step of actually feeding the collected and generated data to the digital model in order to derive output information (e.g. predictions, physiological or anatomical parameters) from the model.

In accordance with one or more embodiments, the processor arrangement may be further configured to perform a further comparison between the generated output information (from the digital model) and the particular defined set of output information. Dependent on the result, the system may be configured to adjust the virtual data generated by the virtual sensing module and/or adjust operation settings of the available physical sensors for example. Additionally or alternatively, dependent on the result, the system may be configured to adjust certain settings of the digital model itself so as to achieve a better match between the output information generated by the digital model and the defined set of required output information.

In accordance with one or more embodiments, the processor arrangement may be configured to modify the set of input information to be provided to the digital model, i.e. determine an alternative input data set which may be provided to the digital model while still permitting the output information requirements to be met. This may be determined for example based on the comparison between the available physical data and the model input data requirement, on the further comparison mentioned above between the output data from the model and the output data requirements and/or on feedback from the virtual sensing module. Based on this, or other factors, the processor arrangement may determine using the digital model an alternative or modified set of input information which may be provided to the digital model, in order to obtain said output information.

For example, the alternative or modified set of input information may be modified to be better matched with the available physical and/or virtual sensor data.

Typically, more than one set of input information is able to realize the output information, i.e. there is typically not a one-to-one relationship between input information and output information. There is hence a degree of freedom available in the model to adjust the input information provided to the model while still allowing the desired outputs to be computed. The system may take advantage of this freedom to adjust the input data requirements to be better suited to the physical or virtual data which is available for example.

This may be based for instance on adjusting one or more operation settings or model parameters of the digital model so that it is able to receive a modified set of input information while still generating the required defined set of output information. For example, a precision level or resolution level of the model might be reduced or otherwise modified, so that less input sensor data needs to be provided or a different set of sensor data can be provided.

This may be done on a recurrent or iterative basis, with the input data requirements adjusted for instance based on feedback gathered on each new run of the steps performed by the system to generate the output data from the model.

By way of example, a feedback loop may be implemented between the various one or more comparisons, and the digital model, and the virtual sensing module, such that the various data collection parameters of the system can be together intelligently configured to collectively optimize the gathered input data and the resulting output data.

For example, feedback streams or a feedback loop may be implemented between the result of the comparison between the available physical data and the model input data requirement, the virtual sensing module, the digital model, and/or the result of the further comparison mentioned above between the output data from the model and the output data requirements, in order to iteratively or recursively adjust one or more of:

the physical sensor data acquired from the physical sensors the virtual sensor data generated by the virtual sensing module, operation settings of one or more of the physical sensors, and/or operation settings and/or model parameters of the digital model.

In embodiments of the invention, adjustment for the physical sensors may relate to collected signal properties, such as sampling frequency, time and frequency of collection, noise reduction, sensor temperature, sensor power consumption, sensor battery level, estimated sensor discomfort, sensor use or not use, etc.

Adjustment for the virtual sensor data may be determined based on the difference between optimal (or desired or pre-programmed) physical sensor settings (including physical sensors data characteristics) and actual physical sensor settings and data. Depending on the characteristics of the incoming physical sensor data, the processing performed on the data will change. For instance, if a sensor is off, the missing data can be synthesized, if the data is missing or of low quality, it can be generated and improved, etc. Also, the adjustments done by the virtual sensing module depend on type of the sensor data collected. Fusion/Processing of PPG and temperature data, will be different that fusion of respiration and blood pressure data for example.

Adjustment of operational settings of physical sensors can be as a result of the above comparisons. They may be based on the error signal generation (i.e. comparisons) for input data, as well as physical sensor types, configuration, use protocols, permissions, etc.

In accordance with one or more embodiments, the processor arrangement may be configured to execute an initial phase in which only a subset of available physical sensors is activated for data collection, and at least a further phase in which, based on performing a further comparison between resultant output information from the model using the subset of sensor data and the particular defined set of output information, a modified subset of the physical sensors is activated.

Thus, in this set of embodiments, initially only a subset of sensors is activated, and, based on feedback as to performance of the digital model in generating the required output information, subsequently, the particular set of activated sensors can be adjusted (e.g. iteratively, through multiple runs of the model) to better meet the data requirements for generating the desired output information. The initial phase and further phase may optionally both be implemented during an initialization or set-up period or mode of the system, in which accurate and optimized output information from the model is not yet needed.

The same thing may additionally or alternatively be done based on a comparison between a combination of acquired physical sensor data after any adjustment of settings and any generated virtual sensor data, and the required input information. In other words, based on this comparison, an initial set of activated sensors may be adjusted (more sensors activated or a different set of sensors activated) so that the acquired data better meets the input data requirements of the digital model for generating the required output information.

Additionally or alternatively, in either case, instead of adjusting which sensors are activated or deactivated between the two phases, operation settings of one or more of the sensors may be adjusted between the two phases, for instance to activate certain additional features of the physical sensors. By way of one example for instance, in a first phase, sensor X might be run with limited capacity (e.g. 1 Hz sampling frequency) collecting only data type Y, while in the second phase the same sensor X might be adjusted to a higher sampling frequency (e.g. 50 Hz), and collecting data types Y and Z.

In various embodiments, use is made of physical sensors of different types (e.g. blood pressure, temperature, and ECG sensor), and different characteristics (e.g. using arterial line, or cuff to measure the blood pressure). In one case, the input set includes physical sensor signals, and as well as some physical sensor signals replaced by the virtual signals. Depending on an error signal from a comparison of the outputs, a set of physical sensors active (and their characteristics) can change, and this will result in different virtual signals. In other words, the modified subset refers to the set of physical sensors from which data is collected for the generation of the output.

In accordance with an advantageous set of embodiments, the processor arrangement may be configured to perform a further comparison between:

a combination of acquired physical sensor data after any adjustment of settings and any generated virtual sensor data, and the required input information.

Based on the result, the operation settings of the physical sensors, and/or the virtual data generated by the virtual sensing module may be adjusted so as to, in combination, better meet the input data requirements of the model. This comparison may be performed either in advance of, or in parallel with, provision of the input data to the model. The adjustments mentioned may be performed for instance ready for implementation in a next run of the steps of the processor arrangement. A comparison between the output data generated by the model using some combined input data might also be performed. Both of these results might be used in combination to inform any adjustments to the operation settings of the physical sensors or the virtual data generation.

The defined set of output information (i.e. the output information requirements) may be user defined, for example received by the processor arrangement from a user interface device.

For example, the processor arrangement may be configured to receive an input indicative of the defined set of output information before the determining of the required input information for the model, for example received from a user interface. The system may include a user interface or a user interface may be external to the system and communicable with the system.

The defined set of output information may in other examples be derived from a different source. For example, it may in some cases be simply read from a dataset or database (e.g. a look-up table), or may be received as an input from a remote server or computer, or may be defined or determined by a local algorithm or program, e.g. an artificial intelligence algorithm, e.g. a machine learning algorithm.

In accordance with one or more embodiments, the system may comprise a plurality of physical sensors communicatively coupleable in use with the processor arrangement for supplying said physical medical sensor data, i.e. the system may include the physical sensors.

The physical sensors may include vital sign sensors such as a heart rate sensor, blood pressure sensor, SpO2 sensor, respiration sensor, ECG sensor, PPG sensor, and/or temperature sensor. The physical sensors may also include medical imaging sensors or devices such as ultrasound sensors or probes, e.g. long-term monitoring probes or sensors.

Examples in accordance with a further aspect of the invention provide a method, comprising:

accessing a digital model of at least part of an anatomy of a patient, the digital model configured for simulating a physical state of said at least part of the anatomy based on adjustment of a set of one or more model input parameters, and the model operable to provide output information related to the simulated physical state of the anatomy; determining from the digital model a required set of input information for providing to the digital model in order to obtain, based on running simulations on the digital model, a particular defined set of output information from the model;

determining an indication of currently available sources of physical sensor data from physical patient sensors;

performing a comparison of the required set of input information and the available sources of physical sensor data; and based on a result of the comparison, generating supplementary data to supplement or replace the physical sensor data, and adjusting one or more operation settings of available physical sensors, for improving a match between the available data and the required input information.

The generating the supplementary data may be based at least in part on processing of received physical sensor data. However, it may alternatively be based on other sources. For example, it may be based at least in part on previously obtained virtual sensor data. It may be based on one or more algorithms or equations or programs for estimating certain types of patient data, for example to replicate physical sensor data but without the need for the physical sensor to be operational. These options will be described in further detail to follow.

The method may further comprise the step of generating output information from the digital model using the physical sensor data and/or virtual sensor data as input information to the digital model.

In accordance with one or more embodiments, the method may further comprise performing a further comparison between the generated output information and the particular defined set of output information.

In accordance with one or more embodiments, the method may further comprise, based on the comparison between the required set of input information and the available sources of physical sensor data, the further comparison mentioned above between the generated output information and the output information requirements, and/or on feedback from the virtual sensing module, determining using the digital model an alternative or modified set of input information which may be provided to the digital model, in order to obtain said output information. This option was explained in more detail above, in relation to the system aspect and these explanations also apply for this method embodiment.

In accordance with one or more embodiments, the method may further comprise performing a further comparison between: a combination of acquired physical sensor data after any adjustment of settings and any generated virtual sensor data, and the required input information.

Examples in accordance with a further aspect of the invention provide a computer program product comprising code means configured, when run on a processor, the processor being communicatively coupled with a data storage arrangement storing a digital model of at least part of an anatomy of a patient, the digital model configured for simulating a physical state of said at least part of the anatomy based on adjustment of a set of one or more model input parameters, and the model operable to provide output information related to the simulated physical state of the anatomy, to perform the method in accordance with any of the examples or embodiments outlined above or described below or in accordance with any claim of this application.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
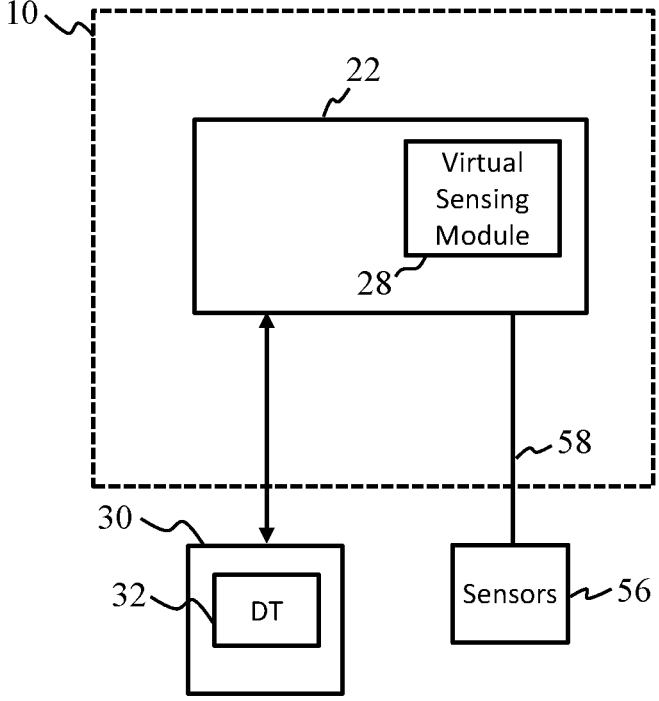
FIG. 1 shows in block diagram form components of an example system in accordance with one or more embodiments of the invention.

The invention will be described with reference to the Figures. It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

A digital twin of a patient offers a clinician advanced interactive visualization and physical insights of relevant health information of the patient. Combining visualization with predictive models that provide projections of future health status and outcome of medical interventions results in personalized clinical decision support to improve diagnostics, treatment selection and interventions. A digital twin can be considered as a "living" digital copy of a real object, such as a patient (or patient organ) being monitored by a patient monitor. In one example, the model receives Personal data: EMR, sensor data, imaging data, etc.

Population data: including data from other people (other than the "real object")

Human intelligence: input provided by human users, such as parameter value settings, data requirements, simulation settings, usage planning, etc., and uses machine learning and AI, deep learning, biophysical modelling, etc.

to provide as outputs

Quantification of past and current status, longitudinal risk assessment

Prediction of future status, prediction of outcomes, and providing recommendations.

A digital twin may have all, or only some of the components stated above, or different components.

The invention provides a system for configuring data collection for provision to a digital twin for generating a desired set of output information (e.g. physiological or anatomical parameter estimations) from the digital twin. The system is configured to detect available sources of physical sensor data pertaining to a patient and to compare these with determined input data requirements of a digital twin of the patient for computing a particular defined set of required output information. Depending on the result, a virtual sensing module can be used to generate supplementary 'virtual' sensor data to compensate for any insufficiencies in the available physical sensor data and/or the system can re-configure operating settings of the available physical sensors to optimally meet the input data requirements of the digital twin.

Various advantageous further features can be applied in particular embodiments for improving the match between acquired input data and the needs of the digital model (the digital twin). For example, comparisons can be made between actual output information generated by the digital model and the output data requirements, and/or between the total combined physical and virtual sensor data and the determined input data requirements of the model. The virtual data generation and/or physical sensor operation settings may be iteratively or recursively adjusted through multiple runs of the system steps, using feedback from each run from the various checks and comparisons, in order to iteratively converge toward an optimum set of collected data for providing to the digital model to obtain the desired output information from the model.

FIG. 1 shows a schematic diagram of the main components of an example system 10 according to one or more embodiments.

The system comprises a processor arrangement 22 communicatively coupled to a data storage arrangement 30 which stores a personalized digital model 32 of at least part of an anatomy of a patient. The data storage arrangement is shown as outside of the system 10 itself in the example of FIG. 1 (i.e. not part of the system) but in alternative examples, the data storage arrangement may be included as part of the system of the invention.

The digital model 32 is configured for simulating a physical state of said at least part of the anatomy based on adjustment of a set of one or more model input parameters. The model is operable to provide output information related to the simulated physical state of the anatomy, for example one or more output parameters. These may correspond to physiological or anatomical parameters of the patient.

The processor arrangement 22 is communicatively coupleable in use with a set of one or more physical patient sensors 56 to receive physical patient sensor data 58. The physical sensors may be outside of the system (as illustrated in FIG. 1) or in alternative examples may be comprised as part of the system of the invention.

The processor arrangement 22 includes a virtual sensor or sensing module 28 configured in use for generating supplementary data. This may be based at least in part on processing of received physical sensor data 58, or may be derived from another source or by another means.

In use, the processor arrangement 22 is configured to perform the following steps:

determine information indicative of currently available sources of physical sensor data 58 obtainable from physical patient sensors 56;

determine from the digital model 32 a required set of input information for providing to the digital model in order to obtain, for example based on running simulations on the digital model, a particular defined set of output information from the model;

perform a comparison of the required set of input information and the available sources of physical sensor data 58;

based on a result of the comparison, use the virtual sensing module 28 to generate supplementary data to supplement or replace the physical sensor data, and to adjust one or more operation settings of available physical sensors, for improving a match between the available data and the required input information.

As used in this disclosure, the digital model (or digital twin) may be understood to be a data and model driven system that receives physical and/or virtual data as an input and generates one or more outputs. In typical use, the digital model is activated (i e running simulations replicating the real-physical state of the patient anatomy) with various inputs, and the variation in the output is observed or analyzed. The digital model output can be used to assess the current patient condition, or to predict future conditions. It may also be used to quantify the predictive value of the digital model output for past conditions (i.e. by using the past input data, generating output information, and comparing the output information with the past observed condition).

As an alternative to the typical operation outlined above (i.e. feeding input information to the digital model 32, running digital model simulation(s), and monitoring the resulting output), it is also possible to use the model algorithms to predict in an 'opposite direction.' In other words it is possible to specify the desired (types of) output information or characteristics (e.g. predicting the patient condition in 24 hours, evaluating the risk of atrial fibrillation, assessing the heart condition, predicting the effect of drug X, etc.) and/or specific data quality requirements (e.g. accuracy, confidence interval), and use the model to indicate the required (types and/or quality of) input information for feeding to the model in order to generate the specified output.

Depending on the set output specifications, input information requirements can be (automatically, or semi-automatically) determined.

Deriving the input information requirements from the output information requirements may be done in various ways.

In accordance with one example, it may be rule based, meaning that there is a simple rule-based relation between desired output information and the necessary input information. Information indicative of which inputs are necessary for which outputs may be specified in a look up table accessible to the digital model for example, or selected based on set rules, or clinical guidelines.

In accordance with further examples, it may be based on learned relations between output information and required input information. For example, it may be learned based on previously run digital twin simulations (e.g. input and output history).

It may be learned in examples based on running test simulations, wherein various different simulations are run with varying input information, and seeking a particular known output. For each test simulation an error is recorded between the obtained output and the desired output and from this it can be learned which set of input information (e.g. types and quality) arrives most closely at the desired output (e.g. optimal set of inputs that are needed to get the minimum error). The results of this learning process can be stored, for example in a database, which may be later consulted to derive the required input information characteristics based on a particular required set of output information.

As discussed above, in addition to specifying the particular required type(s) of output information (i.e. which parameters, measurements, predictions), the quality or other characteristics of that information may also be specified, and the necessary input information characteristics determined by the digital model. These quality characteristics may include, by way of example, a precision level of the generated output values, an estimated accuracy level of the derived output values (e.g. confidence level), and/or a frequency of data value calculation.

Further to quality characteristics for the output information, according to one or more embodiments, there may be specified one or more constraints on the input information characteristics or requirements to be determined by the model. These constraints might include for instance an optimum (e.g. minimum) number of physical sensors to be active, an optimum (e.g. minimum or maximum) power usage by the physical sensors and/or an optimum (e.g. minimum) rate of data generation.

The constraints may additionally or alternatively include a particular data redundancy level, e.g. to enable checks against erroneous or corrupted data. For example, a redundancy level may be defined such that, in use, every physical sensor signal may be recovered (in lossy or lossless manner) by a combination of data from other sensors. The recovery requirements can be set so that lossless recovery is possible, for instance if the sensor signal is of critical importance, or they may be set to enable lossy recovery, if the digital twin can tolerate some degree of error related to the sensor signal to be recovered.

The processor arrangement 22 includes a virtual sensing module 28. The virtual sensing module 28 is operable to generate supplementary data to supplement or replace the physical sensor data 58. The virtual sensing module may be a data and model driven system.

In preferred examples, the virtual sensing module 28 may perform the function of determining, based on comparison between the input data requirements for the digital model 32 and the detected available sensor data, whether and how operation settings of the physical sensors 56 may be adjusted to better meet the input data needs and/or to determine whether and what types of virtual data should be generated. However, this is not essential and another component of the processor arrangement 22 may perform this function.

For example, the virtual sensing module 28 may be operable to detect or to receive, as an input, information indicative of available physical sensors 56 and optionally also various possible operation settings of each of those sensors. For example, it may receive (multiple) physical sensors settings, (multiple) sets of physical sensor data from the various sensors, generated with multiple sensor settings and multiple sensors. It may run calculations (i.e. simulations) to determine if there is redundancy that can exploited to reduce operation of physical sensors (to save power and processing resource), or if new information not available from the individual sensor signals may be calculated by combination of information from multiple sensors.

One of the outputs from the virtual sensing module 28 may include feedback indicative of proposed new physical sensor operation settings for configuring the available physical sensors to collect particular types of data and optionally at a particular quality level or at a particular frequency (in order to meet the input data requirements for the digital model 32). The optimum physical sensor settings may be arrived at iteratively, for example through an adaptive learning loop, through performing multiple runs of the digital model 32 simulations, and seeking to optimize the collected input data. These may for instance be performed as trial runs before true operation begins As will be discussed below, there may be provided a separate physical sensing module in communication with available physics sensors 56. The virtual sensing module 28 may output feedback to the physical sensing module (as part of an adaptive learning loop) and the physical sensing module may adjust operation settings of the sensors based on the feedback. The virtual sensing module 28 may be a separate processor component or may represent merely a functionality of a single central processing component, i.e. it may be a figurative or functional module. For ease of reference, it will be referred to as a separate module, but it is to be understood that this is merely by way of example.

As mentioned, the processor arrangement 22 may further include a physical sensing module (not shown in FIG. 1) for communicating in use with any one or more physical medical sensors 56 to receive physical sensor data 58. It may also perform the function of the processor arrangement of comparing the required set of input information with the available sources of physical sensor data.

By way of example, a physical sensor module may include a model-driven system configured to receive as inputs the input information requirements of the model and feedback from the virtual sensing module. Based on these inputs it may perform the function of determining any adjustments to the operation settings of the available physical sensors for improving a match between the available data the required input information of the model.

For example, the physical sensor module may be configured to use a locally encoded model (or network of models) to determine optimum (individual or network) physical sensor settings for best meeting the input information requirements of the digital model.

In some examples, the physical sensing module may take the form of a digital twin of an individual physical sensor, or may embody digital twins of the complete set of available physical sensors.

The physical sensing module may be configured for determining the limitations or capabilities of the physical sensors communicable with the system 10 relative to the input information requirements of the digital model 32, and relative to the proposed sensor setting changes generated by the virtual sensing module. In other words, physical sensing module may provide an interface between the physical sensors and the remaining components of the system and may be configured to ensure that a physical sensor (or network of physical sensors) can fulfil an assigned role (i.e. a required type, frequency and quality of data to be collected), by ensuring that the role is assigned within capabilities (or limitations) or the physical sensors.

As with the virtual sensing module, the physical sensor module may be a separate processor component or may represent a functionality of a single central processing module, i.e. it may be a figurative module. For ease of reference, it will be referred to as a separate module, but this represents merely one example.

Although the above has been described in terms of presence of a dedicated physical sensing module, this is not essential and the functionality attributed to it may be performed by another one or more components of the system in other examples.

Furthermore, in some examples, the physical and virtual 28 sensing modules may be provided as a single integral module, in interaction with the digital twin 32. In further examples still the physical and/or virtual sensing modules may be part of the digital twin itself.

The processor arrangement 22 of the system 10 may take any suitable shape. The processor arrangement may for example comprise one or more processors, processor cores or the like that cooperate to form such a processor arrangement. It may consist of a single component, or its functions may be distributed among a plurality of processing components.

As discussed, embodiments make use of a personalized digital model 32 of at least part of the anatomy of a patient. This may be referred to in this disclosure as a digital twin.

Such a digital twin typically provides a model of both the elements and the dynamics of the at least portion of the anatomy of the patient (i.e. the physical twin). The digital twin may by way of example integrate artificial intelligence, machine learning and/or software analytics with spatial network graphs to create a 'living' digital simulation model of the at least portion of the patient's anatomy. By way of non-limiting example, the at least portion of the patient's anatomy may be a part of a lumen system of the patient (e.g.

vascular or digestive systems), such that the digital twin comprises a model of this part of a lumen system of the patient. Such a living digital simulation may for example involve the use of a fluid dynamics model, a systemic model, a tissue deformation model and/or a fluid-structure interaction model in order to develop or update the digital twin based on received sensor data indicative of parameters of a physical state of the patient.

In other words, sensor data (physical or virtual) may be used to update and change the digital twin dynamically, and optionally in real time, such that any changes to the patient as highlighted by the data are reflected in the digital twin. As such, the digital twin forms a learning system that learns from itself using the sensor data. The digital twin is thus preferably a dynamic model which dynamically develops or updates so as to provide an accurate representation of the patient's real anatomy.

The biophysical model 32, i.e. the digital twin, of the patient may be initially developed from patient data, e.g. imaging data such as CT images, MRI images, ultrasound images, and/or physical sensor data such as vital sign data. For example, a medical scan may be conducted of the patient, and/or a set of one or more physiological or anatomical parameter measurements taken for the patient, and the digital model constructed based on this.

A typical workflow for creating and validating a 3D, subject-specific biophysical model is depicted in "Current progress in patient-specific modeling", by Neal and Kerckhoff, 1, 2009, Vol. 2, pp. 111-126. For example, in case of a digital twin representing part of the cardiovascular system of the patient, such a biophysical model may be derived from one or more angiograms of the patient. For example, sensor data produced by the sensors may be used to continuously or periodically update the boundary condition of a flow simulation through the digital lumen model (i.e. the digital twin) of the patient.

In operation, the processor arrangement 22 may develop or update the digital twin using received sensor data or virtual sensor data in order to simulate the actual physical state of the at least portion of the anatomy of the patient.

Development and implementation of digital twin models for various example applications are described in the literature for this field. By way of example, implementation details for various example digital twin models are described in the following papers: González, D., Cueto, E. & Chinesta, F. Ann Biomed Eng (2016) 44: 35; Ritesh R. Rama & Sebastian Skatulla, Towards real-time cardiac mechanics modelling with patient-specific heart anatomies, Computer Methods in Applied Mechanics and Engineering (2018) 328; 47-74; Hoekstra, A, et al, Virtual physiological human 2016: translating the virtual physiological human to the clinic, interface Focus 8: 20170067; and "Current progress in patient-specific modeling", by Neal and Kerckhoff, 1, 2009, Vol. 2, pp. 111-126.

Details are also outlined in "Computational Biomechanics for Medicine", Grand R. Joldes et al, Springer.

In general, the digital model, e.g. of an organ or tissue area of the patient, incorporates a number of different (e.g. heterogeneous) material properties as parameters of the model, which may include blood vessels, muscles, fat, lining tissue, bones, calcified areas, which each have specific (biomechanical) material properties. These material properties form parameters for the model to allow physical development of the anatomy with changing physiological circumstances to be modelled.

In some examples, the fundamentals of a patient-specific digital model for a given patient's anatomy may be developed in advance of a particular procedure for example, such that before the procedure begins, the digital model is an accurate representation of the current physical state of the portion of the anatomy of the patient, and incorporates sufficient information and knowledge about the material properties and physical response characteristics to allow the model to be dynamically evolved or developed or updated.

The parameter values may be obtained for instance from literature and mapped onto the model, or obtained directly from measurements, e.g. elastography, performed on the patient.

The model hence simulates the real physical state of the patient. By feeding the model appropriate input information, the model is able to provide computed output information relating to one or more physiological or anatomical param- eters. This may be based on running certain simulations on the updated model by tuning input parameters of the model, or may be based on using one or more algorithms encoded in the model, based on input information, to computer or derive physiological information about the state of the patient's anatomy.

From an up-to-date digital twin, one or more physiologi- cal or anatomical parameters of the modelled anatomy (output information) can thus be extracted or read off from the model. These may advantageously be parameters which are not directly measurable using sensors in real time, so that the model provides an insight into physical parameters beyond those that can be measured using standard sensors or imaging equipment.

Figure 2:
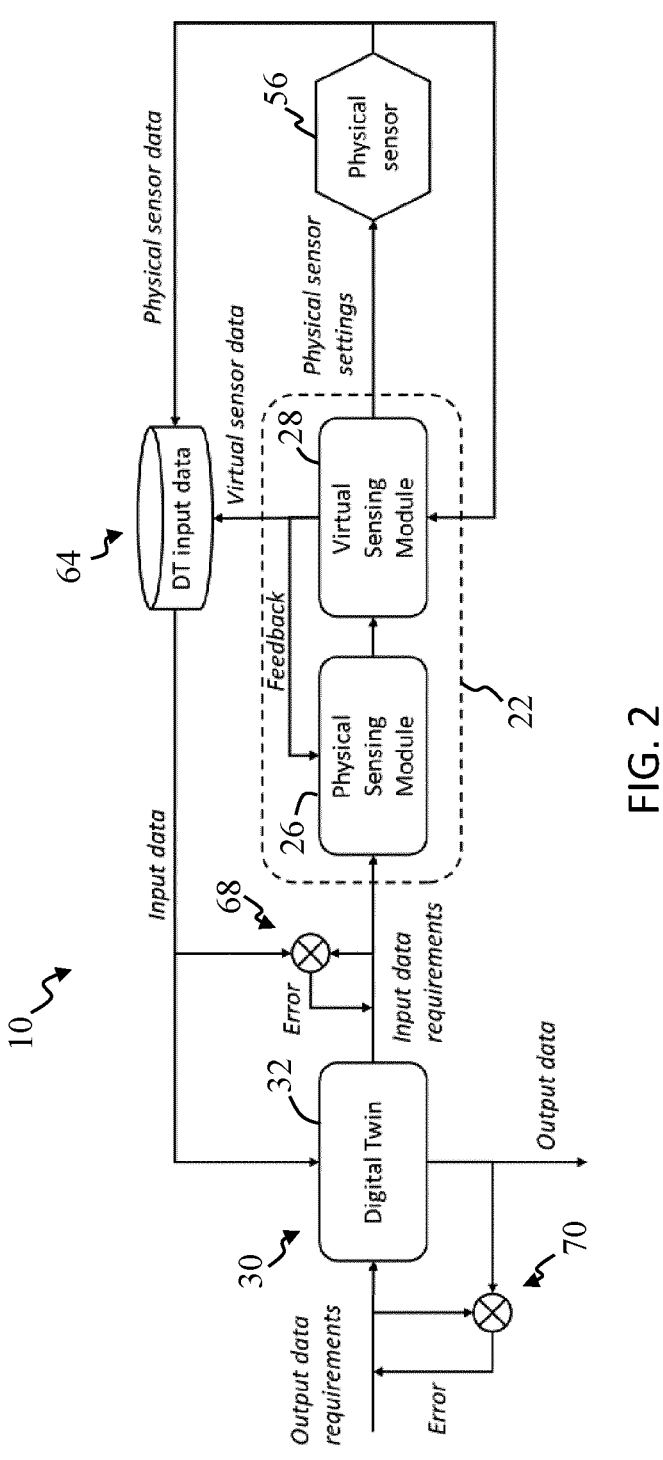
FIG. 2 shows a flow diagram illustrating components and operation of an example system according to one or more embodiments of the invention.

FIG. 2 schematically illustrates in flow diagram form components and functions of an example system 10 in accordance with one or more embodiments of the invention. The processor arrangement 22 is indicated, and is shown, by way of illustration, as including a physical sensing module 26 and virtual sensing module 28 (as discussed above). A data storage arrangement 30 is shown which, in use, stores a digital model 32 of at least part of an anatomy of a patient. The data storage arrangement 30 and processor arrangement 22 are communicatively coupled.

Also shown are a set of physical sensors 56 operatively coupled with the processor arrangement 22, and arranged to receive operation settings from the processor arrangement. The physical sensors 56 are arranged to provide output sensor data back to the processor arrangement 22, where it is combined 64 with virtual sensor data generated by the virtual sensing module 28 before being provided as input information to the digital model (digital twin) 32. Using the provided input information, the digital twin generates a set of output information or output data indicative for example of one or more physiological or anatomical parameters or one or more medical predictions or estimates for instance.

It is noted that in some cases the virtual sensor module may determine that all of the physical sensors may be deactivated (e.g. to save power and processing resource) and their data replaced by virtual data generated by the virtual sensor module, e.g. estimated data. In this case, just virtual sensor data would be provided to the digital model. In other cases, no virtual sensor data might be generated, and so just physical sensor data is provided to the digital twin 32.

As shown, before, or in parallel with, supply of the physical and/or virtual sensor data 64 to the digital twin 32, the combined collected data 64 is compared with the input data requirements earlier determined by the digital twin 32 based on the defined set of output data requirements. Any mismatch between the two is noted and can be used to further improve, in a next iteration or loop of the procedure, the generated virtual data and/or the operation settings of the physical sensors so as to achieve a better match between the combined collected data 64 and the input data requirements for the digital model 32.

After generation of the output information or data from the digital twin 32, the output information may be compared with the pre-defined (e.g. user defined) output data require- ments. Any mismatch is noted and can be used to either adjust the input data requirements set by the digital twin, or to adjust the virtual sensor data which is generated or the operation settings of the physical sensors 56.

In more detail, and with reference to FIG. 2, the procedure followed by the system 10 may, in accordance with one or more embodiments, run as follows.

A particular defined set of output information required from the digital model 32 is received or obtained by the processor arrangement 22. For example, the output infor- mation requirements may be specified by a user, for example by a human operator (e.g. a clinician). They may be input by a user through a user interface and received by the processor arrangement 22 from the user interface. Alternatively, the output information requirements may be specified and com- municated to the processor arrangement from another device downstream from the system 10 which is arranged to receive the output information. Alternatively, they might be speci- fied in accordance with certain clinical guidelines, in which case the processor arrangement 22 itself may look up or determine or retrieve the requirements.

The particular output information requirements are com- municated to the digital model 32, which is configured based on these to determine the required input information for deriving the specified output information. As discussed above the input information requirements may include the types and quality of input information and/or may include frequency or number of input data points.

As discussed above, determining the input data require- ments may be done in different ways. For instance, a lookup table may be referred to. A pre-stored set of digital twin design specifications may be referred to. Alternatively, they may be determined based on running multiple trial simula- tions with varying input specifications, and seeking the set of input data requirements that comes closest to providing the required output information, i.e. which minimize the error between the known desired output requirements and the actual calculated output.

The physical sensing module 26 is in use operatively coupled with a set of physical sensors 56 which may be part of the system 10 or external to the system. The physical sensing module may be configured to detect or determine the set of physical sensors which are currently available for instance based on detecting currently active connections or communication channels.

Based on the determined input data requirements, the physical sensing module 26 determines the (potential) a set of physical sensor 56 settings that may be used (if selected by the virtual sensing module 28) to generate the required input information (or which comes closest to generating the required input information). Hence the physical sensing module generates a proposal for sensor settings which are in accordance with the known sensor (hardware) specifications (e.g. sampling rate, sensitivity, operating temperature, etc.) and which most closely match the required input informa- tion for the digital model 32.

The virtual sensing module 28 may then determine how the physical sensor settings may be modified according to a selected (optimization) criteria, which may change in line with the (real-time) operations or modifications of the digital model 32, while still ensuring that the input data requirements for the model are satisfied. The optimization criteria may take different forms. They may include criteria for improving efficiency of the system, for instance by minimizing the number of active sensors and the rate of data collection while still meeting the input information requirements. This may save power and processing resource.

By way of further examples, the optimization criteria used by the virtual sensing module 28 in determining adjustments to the operations settings of the physical sensors 56 may include one or more of the following making use of each available physical sensor only when needed and in the required capacity, enabling continuous performance and quality checks of the physical sensor data, improving the physical interaction between the physical sensor and the physical object with which it is in mechanical interaction (e g minimizing the discomfort to the subject), acquiring sufficient data to enable generation of new (virtual) data for compensating for missing or inaccurate physical sensor data.

The determined physical sensor operation settings are communicated to the physical sensors 56 (e.g. by the virtual sensing module 28), and physical sensor data is collected.

The virtual sensing module 28 further determines whether further virtual sensing data needs to be generated to supplement physical sensor data in order to meet the input data requirements of the digital model 32. If needed, the virtual sensing module generates virtual sensor data based on processing of the collected physical sensor data (and potentially also archived past that may be available).

The collected physical sensor data and any generated virtual sensor data is combined 64.

A check or comparison (indicated by arrow 68) is then performed to determine whether the combined collected data 64 meets the input information requirements of the digital model. This may be done in advance of running the digital model with the collected input data or in parallel with this.

For example, before providing the combined collected data 64 to the digital model 32 to generate output information (i.e. before allowing DT to use the data), the collected data is compared 68 (e.g. in terms of data types and data quality) to the required input data characteristics. An error signal or error information may be computed indicative of any discrepancies between the input data requirements and the collected data 64. A pre-defined maximum threshold may be set for the error signal, about which the collected data is deemed not to sufficiently meet the input data requirements of the digital model.

If the collected data 64 does not meet the input data requirements, this may result in the procedure or program looping back to the physical 26 and/or virtual 28 sensing module to re-collect the input data, or collect additional input data. In this case, the error signal/information may be used by the virtual sensing module 28 to determine adjustments which may be made to the operation settings of the physical sensors 56, and/or to the types or quality of virtual sensor data which is generated in order to improve the match with the input data requirements. Hence a feedback stream or feedback loop is implemented between the check 68 (between the total collected data 64 and the input data requirements) and the virtual sensing module 28.

Furthermore, the digital twin 32 may also be probed to determine if changes can be made to the input data requirements (while still meeting the output data requirements) in an attempt to achieve a better match between the collected data 64 and the input data requirements. For instance, there is typically not a one-to-one correspondence between output data requirements and a single set of input data which is needed to achieve the output data. Often there may be multiple options for the input data requirements. Feedback from the check 68 and/or the virtual sensing module 28 can be used to probe the digital model 32 for adjustments to the input data requirements. Hence here a feedback stream or feedback loop is implemented between the check 68, the virtual sensing module 28 and digital model 32.

In some embodiments (and as shown by way of illustration in FIG. 2), even where the input information requirements of the digital model 32 are not satisfied (e.g. error for input data is above a set threshold), the collected data 64 may still be passed to the digital model 32 (i.e. the digital model is still allowed to use the collected data), and the digital model 32 runs its simulations based on the received input data to generate output information.

In either case, at some point in the program or procedure, the digital model 32 receives the combined collected data 64 (physical sensor data and virtual sensor data if generated) and, based on this, generates output information.

The generated output information is compared (indicated by arrow 70) with the defined output information requirements and any discrepancy or mismatch noted. As with the input data check 68, an error signal may be computed dependent on the degree of discrepancy and a maximum error threshold set.

Based on the comparison 70 between the output data requirements and the generated output data, feedback may be provided to the virtual 28 or physical 26 sensing modules and/or to the digital model 32 itself. By way of example, based on this feedback, the operation settings of the available physical sensors 56 may be further adjusted and/or the virtual sensor data generated by the virtual sensing module 28 may be altered in order to improve the correspondence between the generated output data and the output information requirements.

In some examples, the feedback from the output information check 70 may be used to inform adjustments to the input data requirements. For instance, as noted above, based on the results of the check 70, the digital model 32 may be probed for an alternative set of input information requirements which still meet the output information requirements, in order to improve the match between generated output data and required output data. Hence a feedback stream or loop may be implemented between: the comparison 70 between the generated output data and the defined output information requirements, the comparison 68 between the collected data 64 and the input data requirements, the virtual sensing module 28 and/or the digital model 32 for iteratively or recursively adjusting data collection settings and parameters to converge toward an optimal collected set of data for achieving the required output information. A learning mechanism may be implemented between these various components and steps of the system for improving correspondence between generated output information and output information requirements, for example while also taking into account any optimization constraints for the physical sensors (as discussed above).

Thus, the input information requirements determined by the digital model 32 and the virtual sensing module 28 control and guide the choice and specifications of the acquired physical sensor data and generated virtual sensor data.

As discussed above, the processor arrangement 22 (e.g. the virtual sensing module 28 of the processor arrangement) is configured to determine operation settings for available physical sensors and also types of virtual data to be collected and the algorithms or methods used to compute the virtual sensor data (from processing of physical sensor data). As discussed, the operation settings for the physical sensors can include which of the full set of available physical sensors is active at a given time and/or a rate of data collected from them. Configurations for virtual sensor data collection can include algorithms or models or relations which are applied for processing physical sensor data to achieve the virtual sensor data.

Some example features and options will now be discussed relating to the determination of physical sensor operation settings and the configuration of virtual sensor data generation.

In accordance with one or more embodiments, the processor arrangement 22 may be configured to alternate periodically between activation and deactivation of a particular one or more physical sensors. In accordance with one or more embodiments for instance, a particular required data type may be generated by the virtual sensing module 28 as virtual sensor data, and wherein the equivalent physical sensor is periodically re-activated to check or corroborate that the virtual sensor data being generated is still in conformity with the true physical quantity. If not, the algorithm or relation used by the virtual sensing module may be updated or corrected.

One example of this will now be outlined in relation to the particular case of deriving physiological strain using a digital model 32 based on inputs of PPG readings and skin temperature. Although described in relation to one particular clinical application, this is for ease of explanation only and it is to be understood that the operating principles underlying this examples may be applied to any desired application to achieve the same or equivalent advantages.

For this example, a digital model 32 is considered which is configured to evaluate (i.e. generate as output information) physiological strain during exercise in heat. Two of the inputs needed for the digital model 32 (among others) are skin temperature and heart rate.

An operating scenario might, by way of example, run as follows.

Between time t0 and t1, skin temperature sensors and PPG sensors (both physical sensors) have been activated in a synchronous manner, and the digital model 32 has used these signals to estimate the patient condition. Also during this time, the virtual sensing module observes the relationship between PPG amplitude and skin temperature for the specific patient, and through this detects and learns a correlation or transfer function between PPG amplitude and skin temperature changes specific for the patient.

Figure 3:
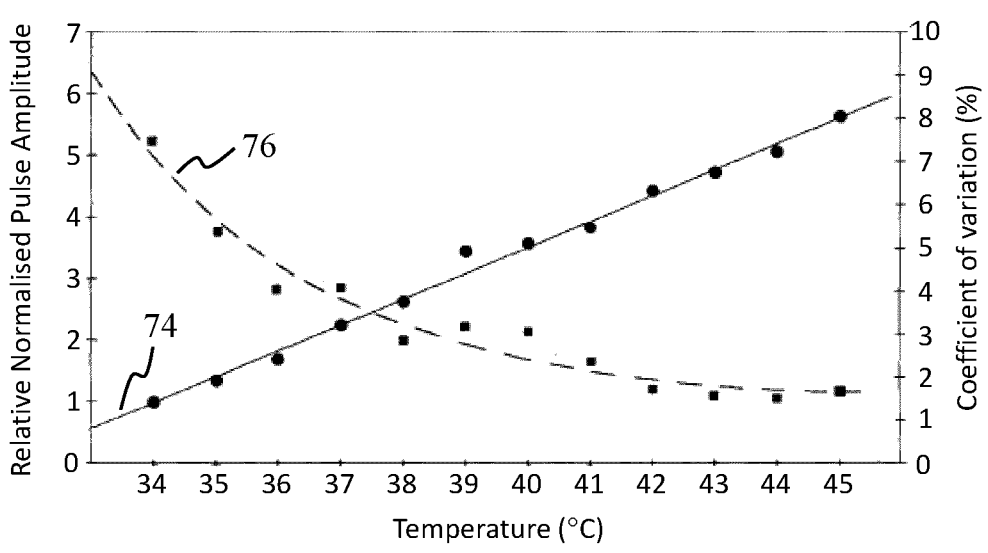
FIG. 3 shows a graph illustrating PPG amplitude variations with temperature and the resulting correlation function.

Note that the link between infrared PPG amplitude changes and skin temperature changes is well established in the field, and these parameters may be highly correlated as shown in FIG. 3. A similar correlation is observable also for red PPG signals (i.e. sub-infrared wavelength). Line 74 shows the trend line between mean PPG amplitude measurements (y-axis, left) and temperature (x-axis, ° C.). The virtual sensing module 28 hence detects the particular quantitative correlation function or relation between them for the particular patient.

Line 74 in FIG. 3 shows the trend in mean pulse amplitude (y-axis, left) as a function of temperature (x-axis, ° C.). As the local skin temperature increases from 34° C. to 45° C. in the illustrated example, it is observed that the mean pulse amplitude (line 74) increases almost five-fold.

Line 76 shows the trend in beat-to-beat pulse amplitude variation (y-axis, right) as a function of temperature (x-axis, ° C.). This corresponds to the beat to beat fluctuations in the photoplethysmogram signal. It can be observed in this example that the PPG signal becomes more stable with increasing temperature, resulting in smaller beat-to-beat amplitude fluctuations (the variation drops from approximately 6.5% to approximately 1% between 34° C. and 45° C.). This is because, by heating the skin, the vascular bed becomes vasodilated, and therefore beat to beat amplitude fluctuations are smaller.

Between time t1 and t2, a trial or test mode is run to test whether virtual sensor data may be generated to replace one of the physical sensors, based on the learned transfer function from one physical parameter to the other. For this, during t1 to t2, the digital model is controlled to generate two outputs, output 1: using the physical PPG sensor and physical temperature sensor as inputs, and output 2: with physical PPG sensor and a virtual temperature signal derived from the PPG amplitude variations using the learned transfer function.

Output 1 and output 2 are compared to see whether their results are in agreement. For the purposes of this example, it is assumed that their results are in agreement, e.g. any differences between them are within a (defined or accepted) error margin.

Following this, at time t3, the virtual sensing module 28 responds by deactivating the physical temperature sensor (for example to save power or to minimize patient discomfort caused by the sensor). An alert that the physical temperature sensors will be disabled may also be provided to the digital model 32 (for example communicated by the virtual sensing module 28). Physical temperature sensors are deactivated at t3.

At t4, the virtual sensing module 28 re-activates the physical skin temperature sensor and the digital model 32 is controlled to re-run the trial or test mode performed in time [t1 t2], to verify that virtual sensor signal is still trustworthy.

For this example, the check is assumed to be positive. Hence, following this, at t5, the physical temperature sensor is switched off again.

At t6, again the trial or test mode performed in time [t1 t2] is repeated to check correspondence between the virtual sensor estimations and the physical sensor readings. It is noted that in one embodiment, the scheduled checks may be performed at regular intervals, and optionally wherein the interval frequency is varied dependent on a condition of the patient. For example, for an unstable patient, frequency of checks may be relatively high, i.e. more often, and for a more stable patient may be lower, i.e. less frequent.

At the check performed at t6, for this example it is now assumed that the check is negative: the physical and virtual sensor outputs do not agree (the digital model 32 outputs generated with the physical and virtual temperature signals differ from each other). Hence, the transfer function (between PPG and temperature) that has been previously learned is no longer reliable (for example, this may be due to a change in the patient condition, or of sensor functionality, or sensor usage).

Depending on the degree of the difference (i.e. the error) or on a type and nature of the clinical output produced by the digital model during [t5 t6], an alert may be generated to inform a clinician that the digital model output between t5 and t6 may be inaccurate.

Continuing with the example, at t7, a new transfer function between the readings of the two physical sensors is established based on monitoring a relation between readings of the two sensors over a given time period. This new transfer function is recorded to replace the previous one. The temperature sensor is then switched off once again.

At t8, the temperature sensor is again switched on and the trial or test mode of [t1 t2] is performed again. T8 may be set at a defined time interval after t7, or it may be chosen based on the digital model predicting or observing a change in a patient condition at this time (e.g. dehydration or heat stroke), this change thereby triggering the re-activation of the skin temperature sensor.

As mentioned above, there are different options as to the particular timings at which physical sensors are chosen to be activated and deactivated. A number of example options will now be discussed regarding the timings for activation and deactivation.

As discussed above, in some examples, the frequency of physical sensor reactivation (and the accompanying accuracy check) may be based at least in part on (past, current or predicted future) patient condition. This may be determined or predicted by the patient digital model 32 for example.

In accordance with one or more examples, the frequency of physical sensor re-activation may be at least partially dependent on the physical sensor settings/specifications or physical properties. For example, it may be known that after a certain usage period, a drift in signal values typically occurs (e.g. due to temperature increase in the sensors). In this case, this known behavior may be taken into account and the activation and deactivation of the physical sensors planned so that the drift is minimal, while at the same time ensuring that patient is reliably monitored.

In accordance with one or more examples, the timings of physical sensor reactivation may be based at least on part on signal features or patterns or fingerprints observed in the physical sensor data and observed to be correlated with unreliable virtual sensor data. For example, presence of certain signal features or patterns, or combinations of features, may be reliably correlated with the corresponding data being unreliable. These relations may be learned in some examples based on use of one or more machine learning algorithms.

In accordance with one or more examples, the timings of physical sensor reactivation may be based at least on part on signal features extracted from the virtual sensor data Similar to above, the virtual sensor signal features can be linked and used to determine the activation schedule. For example, if the virtual sensing module estimates higher temperature values for a period of time, while it is known that for the particular patient such values are highly unlikely, this can trigger immediate activation of the physical sensor.

In accordance with one or more examples, the timings of physical sensor reactivation may be based in part on the particular algorithm used to calculate the virtual data from the physical data. For example, if it is detected that the algorithm has been unable to converge to a single value (as can be the case in machine learning), or boundary (or assumed) conditions known to be necessary for reliable and robust algorithm operation are not satisfied, then the physical sensor may be automatically re-activated in response.

In accordance with one or more examples, the timings of physical sensor reactivation may be rigidly defined, for example codified in legal regulations, or in internal institution regulations. These may be stored in a computer-readable form, and the processor arrangement may refer to these for determining the physical sensor activation timings.

As briefly discussed above, the virtual sensing module 28 in accordance with one or more embodiments, determines operation settings for available physical sensors, and this may be based on one or more optimization criteria. In accordance with one or more advantageous embodiments, the optimization criteria used by the virtual sensing module 28 in configuring the operating settings may be linked with detected changes in patient condition, for example as determined by the digital twin 32. An example will now be discussed.

Two main cases may be considered: (i) improvement in the patient condition, and (ii) deterioration in the patient condition. Different optimization criteria may be applied in each of these cases.

In the first case, where there is an improvement in the patient condition, optimization criteria of: (a) power and lifetime of sensors and (b) comfort of the human subject may be given more weight: The use of the physical sensors for high precision and high frequency monitoring can be relaxed, and some of the physical measurements may be replaced by the virtual measurements. Such an adaptation may help in improving the sensor functionality (e.g. reducing power consumption and extending lifetime), and comfort to the patient (e.g. if blood pressure measurements can be deactivated and blood pressure can be inferred based on other measurements, such as PPG measurements performed at multiple locations).

In the second case, when there is a deterioration in the patient condition (or when the deterioration is expected), the optimization criteria of: digital model performance and robustness, as well as input data quality and reliability may be given more weight. The use of virtual sensors to assess the patient condition can be restricted, and instead physical sensors can be more extensively used. The use of virtual sensors without using the full capacity or full set of available physical sensors may reduce the actual quantity of data that is being collected and therefore increases the risk of missing information. Thus, reducing use of virtual sensors improves reliability and robustness of the data utilized.

In this case, the virtual sensor data may still be computed, but may be used for example mainly to evaluate or corroborate the quality (e.g. robustness, accuracy, consistency, etc.) of the signals gathered by the physical sensors in real-time.

For example, in some cases, it may be possible to extract the same physical information from multiple different physical sensor sources. In this case, virtual sensor values may be used to compare the different sources and eliminate redundant and duplicated signals. For example, the information derived from different sources may be compared to evaluate quality of the physical sensors. For example, the blood pressure and respiration rate calculated from PPG, blood cuff, and respiration belt sensors can compared with each other to decide if the physical sensor data remains reliable.

There can be also cases in which the use of both physical and virtual sensors may be increased. For instance, in the event that, based on the digital model output, a new development in the patient condition is observed, the virtual sensing module 28 may be used to calculate new signals that may be used (at least temporarily) to assess the newly observed condition.

For example, a situation might arise in which a new drug (e.g. Lisinopril) is administered to a heart failure patient (who is being monitored using her heart digital twin). A (rare) side effect (e.g. angioedema of the small bowel) may be observed. In this case, the virtual sensing module might be utilized to generate new data (through processing physical sensor data) that enables monitoring of the side effect, for example, at least until other physical sensors specifically designed to monitor the side effect are available.

In accordance with one or more examples, the use of the physical (/virtual) sensors can be gradually reduced (/increased) based on the observed or expected improvement (/degradation) in the patient condition.

An example clinical case is measurement of the core body temperature in a neuroscience intensive care unit (ICU). In such cases, very accurate core body temperature measurements are required since hyperthermia may have serious effects on the brain. For critically ill patients, fever is associated with poorer outcomes.

For a critically ill patient, one very accurate (but invasive) temperature sensor is a pulmonary artery catheter. This is considered a gold standard, and can obtain continuous temperature measurement. For a less critical patient, a less accurate (+/−0.1°-0.8° C.) but still invasive temperature sensor is a bladder temperature sensor. For general patients, a non-invasive but less accurate (+/−0.9° C.-2.5° C.) temperature sensor is a tympanic temperature sensor.

By way of example, there may be a case in which a bladder temperature is measured. Following this, the virtual sensing module 28 may be used to correct the measurement to be more in line with the pulmonary artery catheter temperature, for instance based on a known or observed relationship between the two (e.g. pulmonary artery catheter temperature ~=bladder temperature−0.2). In this example, the digital model 32 may predict an expected deterioration in patient condition, and therefore increase the input temperature accuracy requirements, resulting in using a pulmonary artery catheter to measure the temperature.

In accordance with one or more advantageous embodiments, the processor arrangement 22 may be configured to perform a checking procedure comprising checking the quality of physical sensor data which is available from the physical sensors.

For some physical sensors, precise positioning on the body is important in order to achieve a high quality sensor reading. If it is known for example that the digital model output is very sensitive to the variations in signal quality, it may be advantageous to perform a checking procedure to check that the input data is of the required minimum quality. The quality criterion may be part of the input information requirements initially determined by the digital model 32.

In some cases, the quality of the data may be readily determined from a determination of the signal to noise ratio. However, in some cases, for example where a potentially misplaced sensor introduces a uniform bias in the sensor data, it may not be possible to determine quality based on analysis of the signal alone. In these cases, other information may be used to check for quality.

For example, the output from some sensors can be used to derive more than one parameter measurement. This redundancy can be used to check the accuracy of a given sensor. For example, if the input information requirements of the digital model 32 require sensor 1 to be of high quality, then the virtual sensing module 28 may extract a second signal, signal 2, from sensor 1, and compare this to a physical sensor measurement of signal 2 from a second sensor, sensor 2. This comparison can be used to verify the reliability of sensor 1.

It is noted that in general the quality requirements for input data may be set statically, i.e. are always the same, but they may also vary, e.g. alternating, for example depending upon digital model 32 simulation settings.

In an example use case, where a PPG sensor (sensor 1) and temperature sensor (sensor 2) are available, and where positioning of the temperature sensor is important, temperature can be extracted from the PPG data (as discussed above) and compared to the real values from the temperature sensor. Any detected differences may be used to quantify if the temperature sensor has been placed (or in general used or functioning) as expected as required by the digital model 32.

Another example use case, is the use of a PPG sensor and a respiration belt. Respiration data can be extracted from PPG data, and compared to the measured respiration data to determine if the PPG sensor has been placed (or is being used or is functioning) accurately.

In accordance with one or more advantageous embodiments, the functionality of the virtual sensing module 28 may be implemented by a further digital twin of the same patient.

For example, the primary digital twin 32 might be a digital twin of the patient's heart, and the virtual sensing module might be a digital twin of lungs of the patient. In this case, the role of the lung digital twin may be to support the heart digital twin by generating virtual sensor data that can be used by the heart digital twin.

Embodiments of the invention thus use a virtual sensing module, which is connected to a digital twin, to drive the operation of the physical sensors. By having the operation of the physical sensors controlled by the virtual sensor, optimal use may be made of physical sensors, without compromising on sensor lifetime and quality of the data collected. Moreover, by fusing data from different types of sensors, new information can be calculated. Interaction of the digital twin with the virtual sensors enables that the virtual sensing operations are determined according to the needs of the digital twin, thus contributing to achieving better care to patients, by improving activities of the clinicians using the digital twin, such as faster and more precise diagnosis and treatment.

Existing virtual sensing definitions (or applications) consider virtual sensors as (AI or machine learning based) software that is able to process and fuse physical sensor data to generate data/signal for physical objects or part of the physical objects (the physical objects are typically structures, like part of a building or machines) that are hard to or impossible to measure using physical sensors directly. There are also definitions that describe data/signals calculated by the digital twins of objects (such as machines) as virtual sensor signals. All of these definitions can be summed as defining the virtual sensor as a software that post-processed physical sensor signals. In other words, the relation is one-directional and the virtual signal generator does not control the operation of physical sensors, only uses it.

In embodiments of the present invention, in addition to using and processing physical sensor signals, a two-way interaction is provided, where the virtual sensor can also influence physical sensor operation. The determination of how this is dependent on the digital twin operations. The aspects of virtual sensing module controlling physical sensor operations and defining the control settings are (i) based on (real-time) digital twin characteristics, or (ii) based on the physical sensor characteristics, or (iii) a combination of (i) and (ii).

Typically, patients are monitored by physical sensors, data collected from the sensors analyzed, and then actions are taken based on the analysis results. Example actions can be (i) patient related (e.g. give drug X), or (ii) sensor related (e.g. increase the sampling frequency with which data is collected), or (iii) data analysis/user interface related (e.g. start displaying/calculating heart rate variability in addition to the heart rate). All of these actions are reactive, i.e. based on the past.

Having a digital twin in the loop enables the future patient status to be predicted. For instance, the likelihood of several future patient conditions can be estimated, such as increase in blood pressure: 0.7, cardiogenic shock: 0.6 etc. Having the potential future conditions predicted, corresponding actions can be taken: (i) patient related: increase monitoring of the patient (generate hemodynamic shock prediction more often), increase number of sensors, etc., (ii) physical sensor related: start storing the raw sensor data, and not only the processed data, (iii) data analysis and user interface related: use virtual sensing to generate "virtual" signals related to the estimated conditions: e.g. estimation of the amount of oxygen delivered to the body tissues (in a specific organ).

The rate at which oxygen ($O_2$) is supplied to the body tissues is the product of cardiac output (systemic blood flow) and arterial oxygen content. Arterial $O_2$ content is a function of arterial hemoglobin concentration, hemoglobin $O_2$ saturation, and the pressure of $O_2$. Systemic $O_2$ is dependent of many factors, such as $O_2$ transport to lungs, blood, and circulation system. In addition, each organ can respond differently to overcome deficiencies in $O_2$ delivery.

In clinical settings, there are situations where a quick or very quick decision is needed (for example when a patient is experiencing a hemodynamic shock). In these emergency situations, certainly the time is the main determinant for how the output can be calculated. In case the patient is stabilized, certainty of the output becomes more important and time becomes less important. There is a continuous trade off between time and uncertainty.

Use of the virtual sensing module can contribute positively to reduce time and uncertainty, by generating (estimating) the relevant information that may be needed, even before all physical sensor data is collected (e.g. if a digital twin requires 60 s of temperature data, the last 30 s can be estimated via the virtual sensor from the first 30 s), and by making sure that the right input is given to the digital twin. For example, in order to enable a faster computation, a reduced order bio-physical model may be selected by the clinician as the model to run in the digital twin. Now, the (input) requirements for this reduced order models may de (slightly) different that the full bio-physical model. But the problem is that, the physical sensors were selected and operated according to the full-model use scenario, which means that the reduced-order model still can be operated, but probably not in an optimal manner Having updated input requirement from the digital twin (due to the bio-physical model change), the virtual sensing module can "fill the gap" but generating new signals, or modifying the physical sensor signals according to the optimal needs of the reduced order model.

In summary, use of the virtual sensing module supports faster and better adaptation of the physical sensor settings for the predicted future patient states, and for the different uses and (on-the-spot) modifications in the settings of the digital twin.

Figure 4:
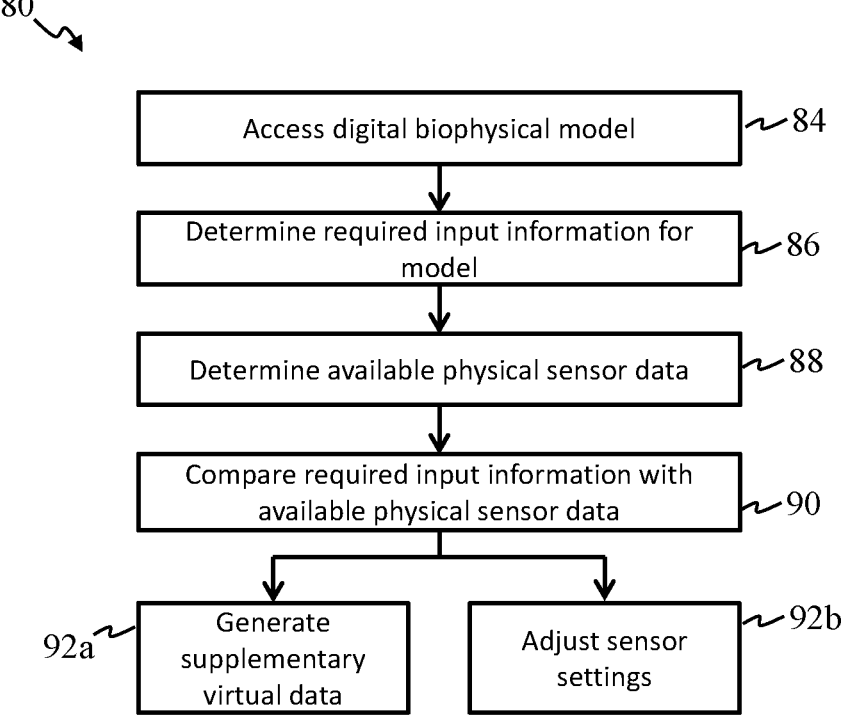
FIG. 4 shows a block diagram of an example method in accordance with one or more embodiments of the invention.

Examples in accordance with a further aspect of the invention also provide a method. An example method 80 in accordance with one or more embodiments is shown in block diagram form in FIG. 4.

The method comprises accessing 84 a digital model 32 of at least part of an anatomy of a patient, the digital model configured for simulating a physical state of said at least part of the anatomy based on adjustment of a set of one or more model input parameters, and the model operable to provide output information related to the simulated physical state of the anatomy.

The method further comprises determining 86 from the digital model 32 a required set of input information for providing to the digital model in order to obtain from the model a particular defined set of output information from the digital model.

The method further comprises determining 88 an indication of currently available sources of physical sensor data from physical patient sensors 56.

The method further comprises performing 90 a comparison of the required set of input information and the available sources of physical sensor data.

Based on a result of the comparison, the method comprises performing: generating 92a supplementary data to supplement or replace the physical sensor data, and adjusting 92b one or more operation settings of available physical sensors, in either case for improving a match between the available data the required input information.

Implementation options and details for each of the above steps may be understood and interpreted in accordance with the explanations and descriptions provided above for the apparatus aspect of the present invention (i.e. the system aspect).

Any of the examples, options or embodiment features or details described above in respect of the system 10 aspect of this invention may be applied or combined or incorporated into the present method aspect of the invention.

For example, the generating the supplementary data may be based at least in part on processing of received physical sensor data. However, it may alternatively be based on other sources. For example, it may be based at least in part on previously obtained virtual sensor data. It may be based on one or more algorithms or equations or programs for estimating certain types of patient data, for example to replicate physical sensor data but without the need for the physical sensor to be operational. Various options in this regard were outlined in more detail above.

Examples in accordance with a further aspect of the invention also provide a computer program product comprising code means configured, when run on a processor, the processor being communicatively coupled with a data storage arrangement storing a digital model 32 of at least part of an anatomy of a patient, the digital model configured for simulating a physical state of said at least part of the anatomy based on adjustment of a set of one or more model input parameters, and the model operable to provide output information related to the simulated physical state of the anatomy, to perform a method in accordance with any example or embodiment described above, or in accordance with any claim of this application.

As discussed above, embodiments of the invention make use of a processor arrangement 22 to perform data processing. As discussed, the processor arrangement may comprise one or more processors. Such processors can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor arrangement may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A system, comprising:
a processor arrangement communicatively coupled to a data storage arrangement storing a digital model of at least part of an anatomy of a patient, the digital model being configured for simulating a physical state of said at least part of the anatomy based on adjustment of a set of one or more model input parameters, and the digital model being operable to provide output information related to the simulated physical state of the anatomy;
the processor arrangement being communicatively couplable in use with one or more physical sensors to receive physical patient sensor data;
the processor arrangement including a virtual sensing module configured in use for generating supplementary data; and
the processor arrangement being configured in use to:
execute an initial phase in which only a subset of available physical sensors are activated for data collection;
determine information indicative of currently available physical patient sensor data from the one or more physical sensors;
determine from the digital model a required set of input information for providing to the digital model in order to obtain, from the digital model, a particular defined set of output information from the model;
perform a comparison of the required set of input information and the available physical patient sensor data;
based on a result of the comparison, use the virtual sensing module to generate supplementary data to supplement or replace the physical patient sensor data:
based on a result of the comparison, adjust one or more operation settings of the one or more physical sensors, for improving a match between the available physical patient sensor data and the required set of input information; and execute a further phase in which, based on performing a further comparison between resultant output information from the digital model using the currently available physical patient sensor data and said particular defined set of output information, activate a modified subset of the physical sensors.

2. The system as claimed in claim 1, wherein the processor arrangement is further configured to generate output information from the digital model using one or more of the physical patient sensor data or the supplementary data as input information to the digital model.

3. The system as claimed in claim 2, wherein the processor arrangement is further configured to perform a further comparison between the generated output information and said particular defined set of output information, to make adjustments to the supplementary data that is generated and the operation settings of the physical sensors.

4. The system as claimed in claim 3, wherein the processor arrangement is further configured to determine based on one or more of the comparison of claim 3, the digital mode or on-feedback from the virtual sensing module, an alternative or modified set of input information formed by the available physical patient sensor data and the supplementary data which may be provided to the digital model, in order to obtain said output information.

5. The system as claimed in claim 3, wherein a feedback loop is implemented between one or more of the result of the comparison, the virtual sensing module, the digital model, or the further comparison of claim 3 in order to iteratively or recursively adjust one or more of the supplementary data generated by the virtual sensing module, and the operation settings of one or more of the physical sensors.

6. The system as claimed in claim 1, wherein the processor arrangement is configured to perform a further comparison between a combination of acquired physical patient sensor data after any adjustment of settings and any generated supplementary data, and the required input information, to make adjustments to the supplementary data that is generated and the operation settings of the physical sensors.

7. The system as claimed in claim 1, wherein the defined set of output information is received by the processor arrangement from a user interface device.

8. The system as claimed in claim 1, wherein the system comprises a plurality of physical sensors communicatively couplable in use with the processor arrangement for supplying said physical patient sensor data.

9. A computer-implemented method, comprising:
accessing a digital model of at least part of an anatomy of a patient, the digital model being configured for simulating a physical state of said at least part of the anatomy based on adjustment of a set of one or more model input parameters, and the model being operable to provide output information related to the simulated physical state of the anatomy;
executing an initial phase in which only a subset of available physical patient sensors are activated for data collection:
determining from the digital model a required set of input information for providing to the digital model in order to obtain, from the digital model, a particular defined set of output information from the model;
determining an indication of currently available physical sensor data from the physical patient sensors;
performing a comparison of the required set of input information and the available physical sensor data;

based on a result of the comparison, generating supplementary data to supplement or replace the available physical sensor data, based on a result of the comparison, adjusting one or more operation settings of the physical patient sensors, for improving a match between the available physical sensor data and the required set of input information; and executing a further phase in which, based on performing a further comparison between resultant output information from the digital model using the currently available physical patient sensor data and said particular defined set of output information, activating a modified subset of the physical patient sensors.

10. The method according to claim 9, further comprising generating output information from the digital model using the physical sensor data or supplementary data as input information to the digital model.

11. The method according to claim 10, further comprising performing a further comparison between the generated output information and the particular defined set of output information.

12. The method according to claim 11 further comprising determining, based on the comparison of claim 11 and using the digital model, an alternative or modified set of input information formed by the available physical sensor data and the supplementary data which may be provided to the digital model, in order to obtain said output information.

13. The method according to claim 9, further comprising performing a further comparison between:

a combination of available physical sensor data after any adjustment of settings and any generated supplementary data, and the required set of input information.

14. A non-transitory computer program product comprising code means configured, when run on a processor, to perform a method, the processor being communicatively coupled with a data storage arrangement storing a digital model of at least part of an anatomy of a patient, the digital model being configured for simulating a physical state of said at least part of the anatomy based on adjustment of a set of one or more model input parameters, and the model operable to provide output information related to the simulated physical state of the anatomy, the method comprising:

accessing a digital model of at least part of an anatomy of a patient, the digital model being configured for simulating a physical state of said at least part of the anatomy based on adjustment of a set of one or more model input parameters, and the model being operable to provide output information related to the simulated physical state of the anatomy;

executing an initial phase in which only a subset of available physical patient sensors are activated for data collection;

determining from the digital model a required set of input information for providing to the digital model in order to obtain, from the digital model, a particular defined set of output information from the model;

determining an indication of currently available physical sensor data from physical patient sensors;

performing a comparison of the required set of input information and the available physical sensor data;

based on a result of the comparison, generating supplementary data to supplement or replace the available physical sensor data, based on a result of the comparison, adjusting one or more operation settings of the physical patient sensors, for improving a match between the available physical sensor data and the required set of input information; and executing a further phase in which, based on performing a further comparison between resultant output information from the digital model using the currently available physical patient sensor data and said particular defined set of output information, activating a modified subset of the physical patient sensors.

\* \* \* \* \*